United States Patent
Kim et al.

(10) Patent No.: US 11,001,860 B2
(45) Date of Patent: May 11, 2021

(54) POXVIRUS-DERIVED PROMOTER, AND VECTOR COMPRISING SAME

(71) Applicant: KOLON LIFE SCIENCE, INC., Gwacheon-si (KR)

(72) Inventors: Sujeong Kim, Seoul (KR); Minjung Kim, Seoul (KR); Hwanjun Choi, Seoul (KR)

(73) Assignee: KOLON LIFE SCIENCE, INC., Seoul (KR)

( * ) Notice: Subject to any disclaimer, the term of this patent is extended or adjusted under 35 U.S.C. 154(b) by 497 days.

(21) Appl. No.: 15/575,470

(22) PCT Filed: May 27, 2016

(86) PCT No.: PCT/KR2016/005647
§ 371 (c)(1),
(2) Date: Nov. 20, 2017

(87) PCT Pub. No.: WO2016/195332
PCT Pub. Date: Dec. 8, 2016

(65) Prior Publication Data
US 2018/0080048 A1    Mar. 22, 2018

(30) Foreign Application Priority Data
May 29, 2015    (KR) .................. 10-2015-0076197

(51) Int. Cl.
*C07H 21/04*    (2006.01)
*C12N 15/00*    (2006.01)
*C12N 15/63*    (2006.01)
*C12N 15/863*   (2006.01)

(52) U.S. Cl.
CPC ......... *C12N 15/8636* (2013.01); *C12N 15/63* (2013.01); *C12N 15/863* (2013.01)

(58) Field of Classification Search
CPC ... C12N 15/8636; C12N 15/863; C12N 15/63
See application file for complete search history.

(56) References Cited

U.S. PATENT DOCUMENTS

| | | | |
|---|---|---|---|
| 5,547,862 A * | 8/1996 | Meador ................ | C12N 15/70 435/320.1 |
| 7,588,767 B2 * | 9/2009 | Szalay ................ | A61K 35/768 424/199.1 |
| 2010/0136056 A1 * | 6/2010 | Panicali ............... | C12N 15/86 424/232.1 |
| 2013/0280170 A1 * | 10/2013 | Szalay ................ | A61K 49/10 424/9.2 |
| 2014/0271549 A1 | 9/2014 | Szalay | |

FOREIGN PATENT DOCUMENTS

| | | |
|---|---|---|
| CN | 101418314 A | 4/2009 |
| JP | 2006-515170 A | 5/2006 |
| JP | 2012-509678 A | 4/2012 |
| JP | 2012-520061 A | 9/2012 |
| WO | 2010/060632 A1 | 6/2010 |
| WO | 2010/102822 A1 | 9/2010 |
| WO | 2012142529 A2 | 10/2012 |
| WO | 2013038066 A1 | 3/2013 |

OTHER PUBLICATIONS

Di Pilato et al. New vaccinia virus promoter as a potential candidate for future vaccine. Journal of General Virology 94:2771-2776, (Year: 2013).*
Liu et al. A natural vaccinia virus promoter with exceptional capacity to direct protein synthesis. J. Virological Methods 122:141-145, (Year: 2004).*
Li et al. A strategy of gene overexpression based on tandem repetitive promoters in *Escherichia coli*. Microbial Cell Factories 11: 19 pages, (Year: 2012).*
Jia et al. Multistage regulator based on tandem promoters and CRISPR/Cas. ACS Synth. Biol. 3:1007-1010, (Year: 2014).*
Liu Xu et al., "Characterization of vaccinia virus promoters and identification of their corresponding cellular transcription factors", Dissertation, Purdue University, Aug. 2002, XP009149389, pp. 1-140 (total 160 pages).
NCBI, GenBank accession No. AY243312.1, Mar. 14, 2006, 74 pages.
NCBI, GenBank accession No. JN654976.1, Jan. 28, 2012, 78 pages.
Pablo D. Becker, et al., "Gene Expression Driven by a Strong Viral Promoter in MVA Increases Vaccination Efficiency by Enhancing Antibody Responses and Unmasking CD8+T Cell Epitopes", Vaccines, 2014, pp. 581-600, vol. 2, No. 3.
Heather E. Eaton, et al., "Characterization of the promoter activity of a poxvirus conserved element", Canadian Journal of Microbiology, 2008, pp. 483-488, vol. 54, No. 6.
Yuqiao Shen, et al., "Fighting Cancer with Vaccinia Virus: Teaching New Tricks to an Old Dog", Molecular Therapy, 2005, pp. 180-195, vol. 11, No. 2.

* cited by examiner

*Primary Examiner* — Quang Nguyen
(74) *Attorney, Agent, or Firm* — Sughrue Mion, PLLC

(57) ABSTRACT

The present invention provides a poxvirus-derived promoter, a vector comprising the same, a method for expressing a transgene using the promoter, and use of the vector in the prevention or treatment of a disease. A promoter according to the present invention can be used for induction of strong expression of a transgene.

20 Claims, 9 Drawing Sheets
Specification includes a Sequence Listing.

[Fig. 1]
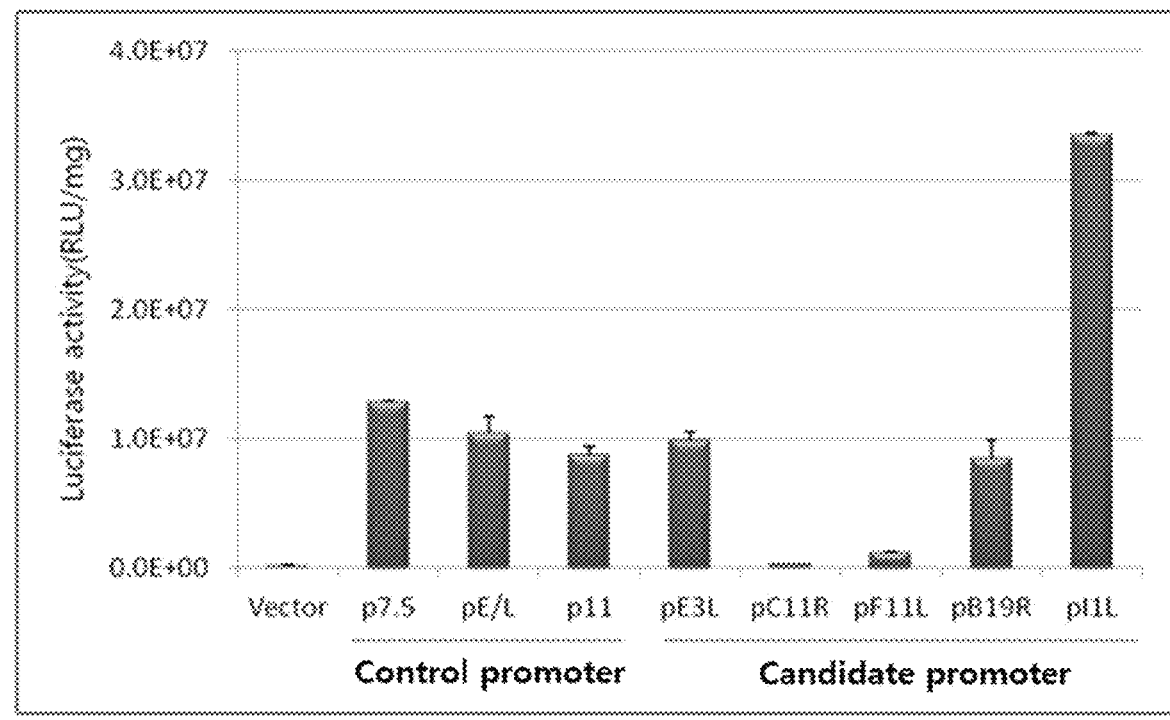
[Fig. 2]
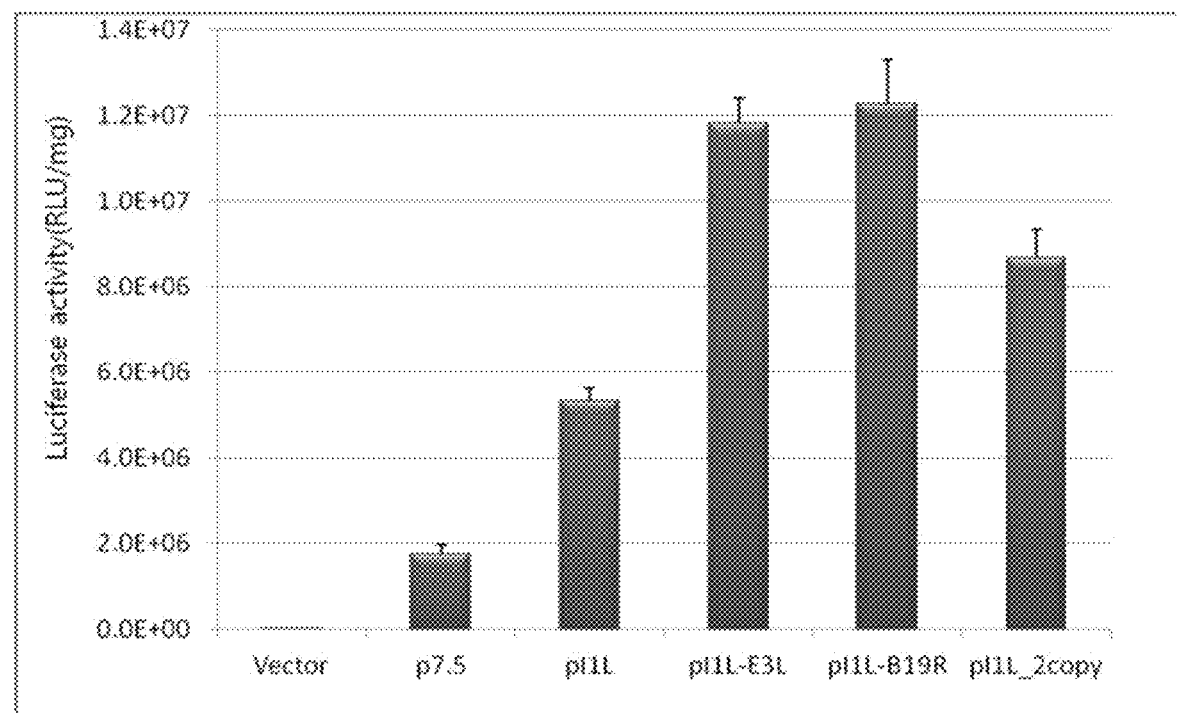

[Fig. 3]
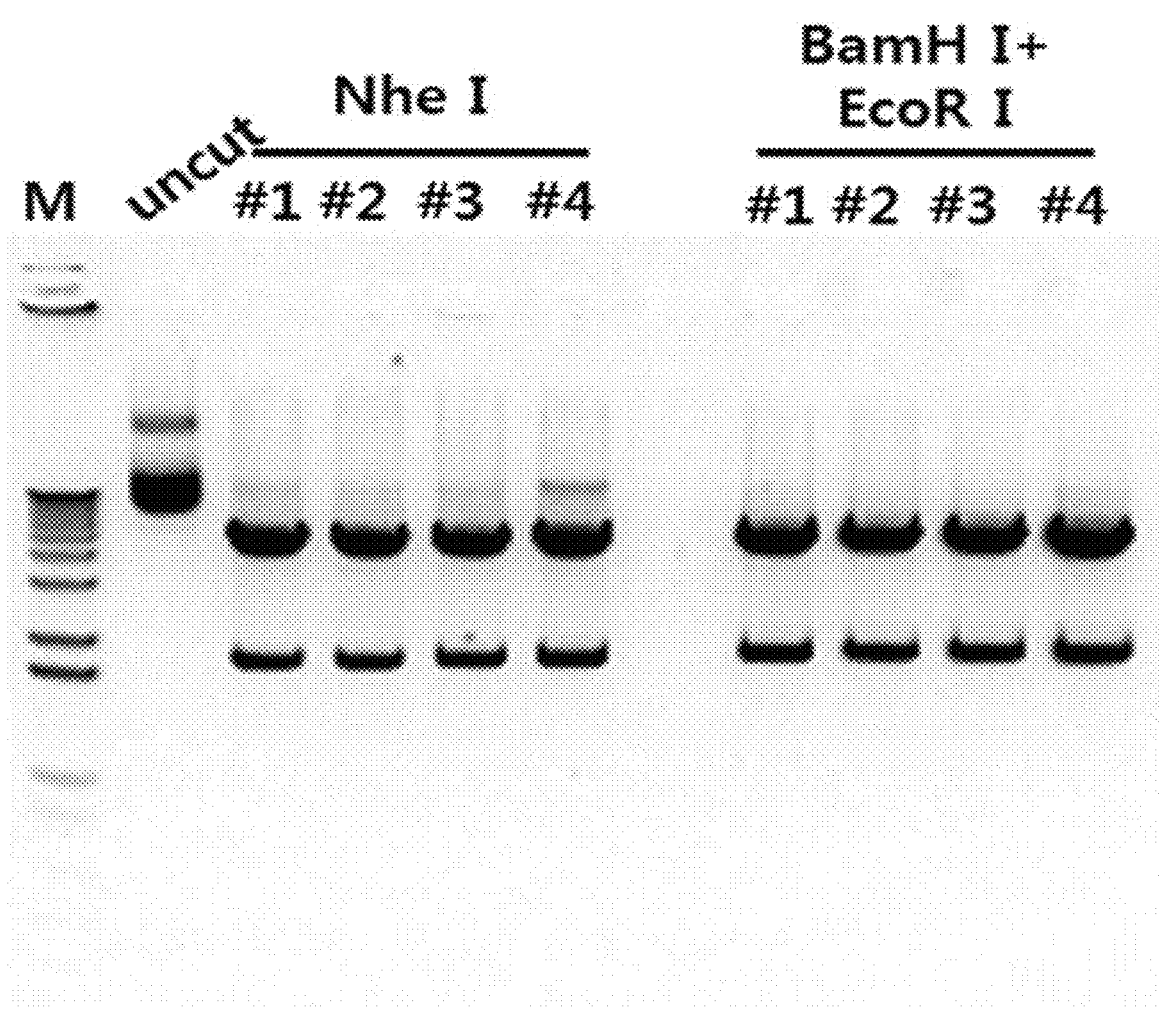

[Fig. 4]
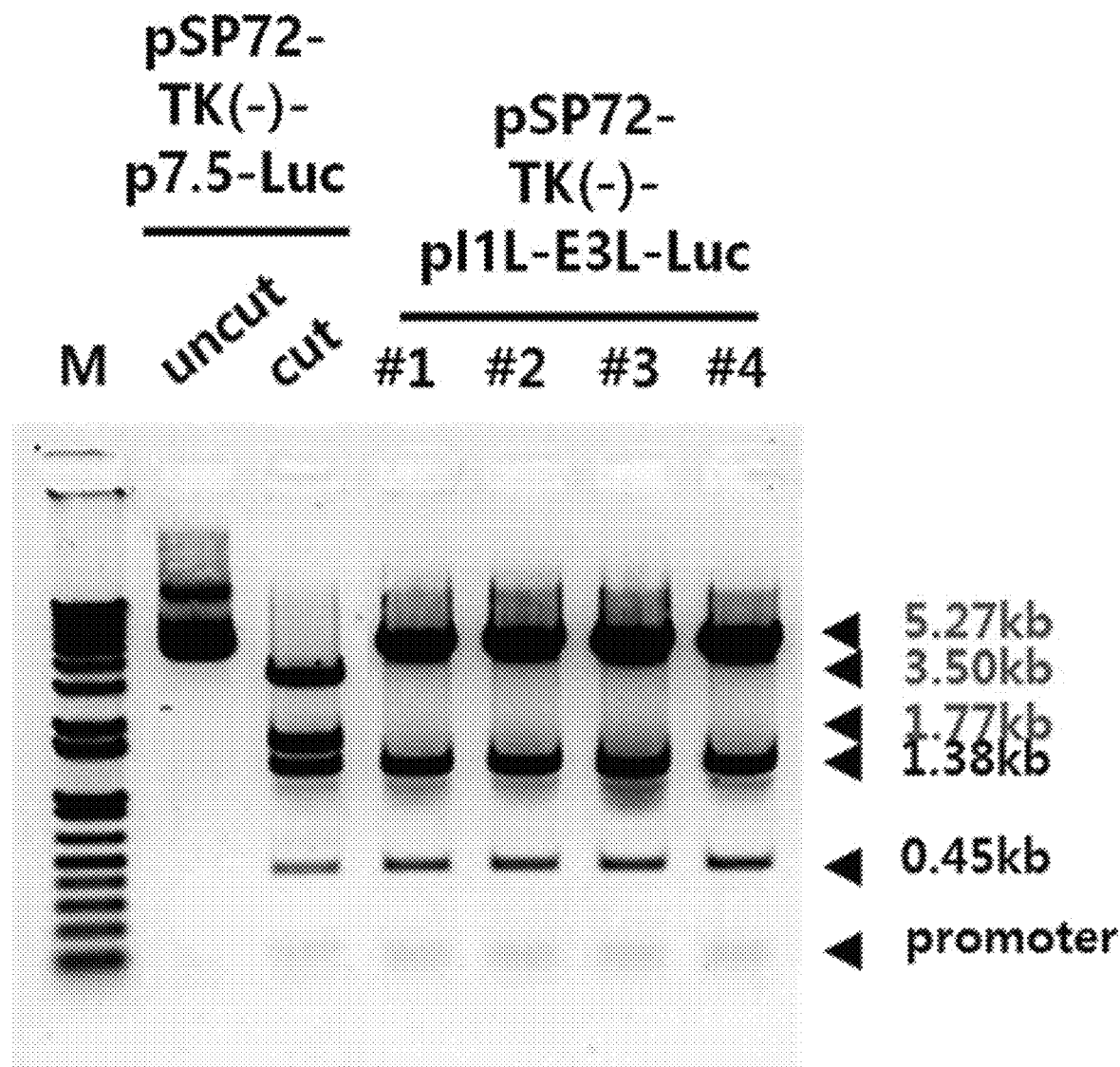

[Fig. 5]
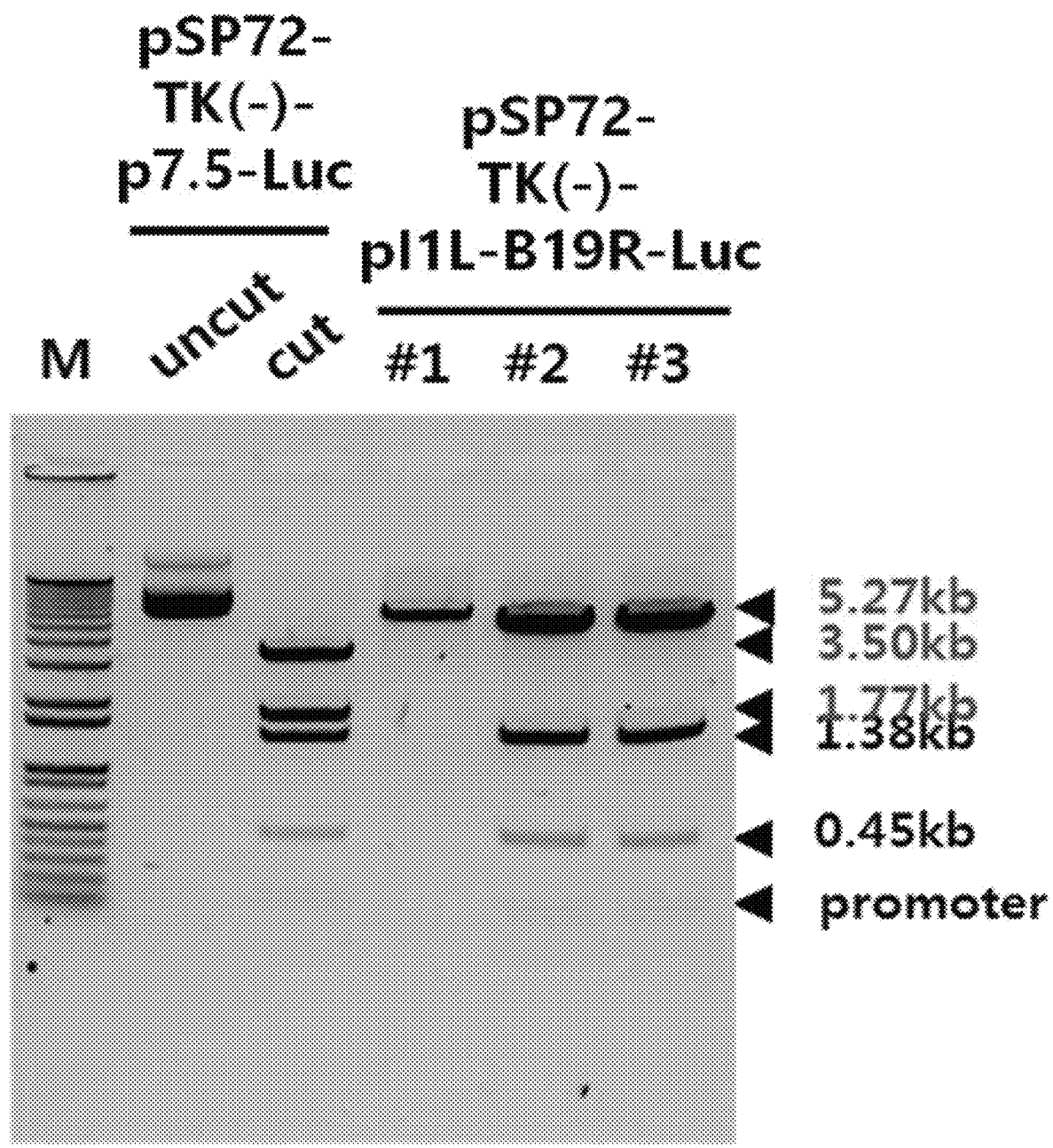

[Fig. 6]
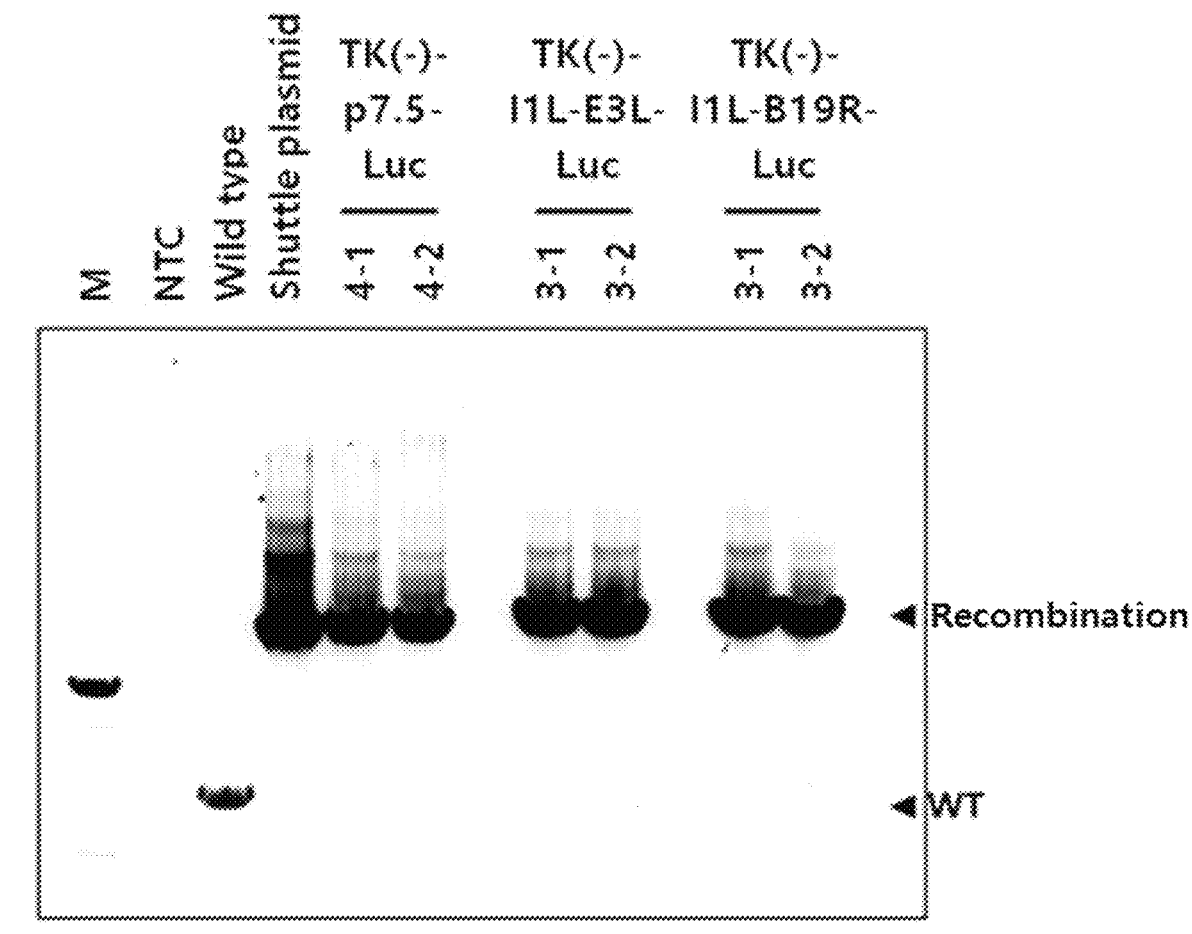
- Wild type : 966 bp
- TK(-)-p7.5-Luc : 3166 bp
- TK(-)-I1L-E3L-Luc : 3127 bp
- TK(-)-I1L-B19R-Luc : 3137 bp

[Fig. 7]
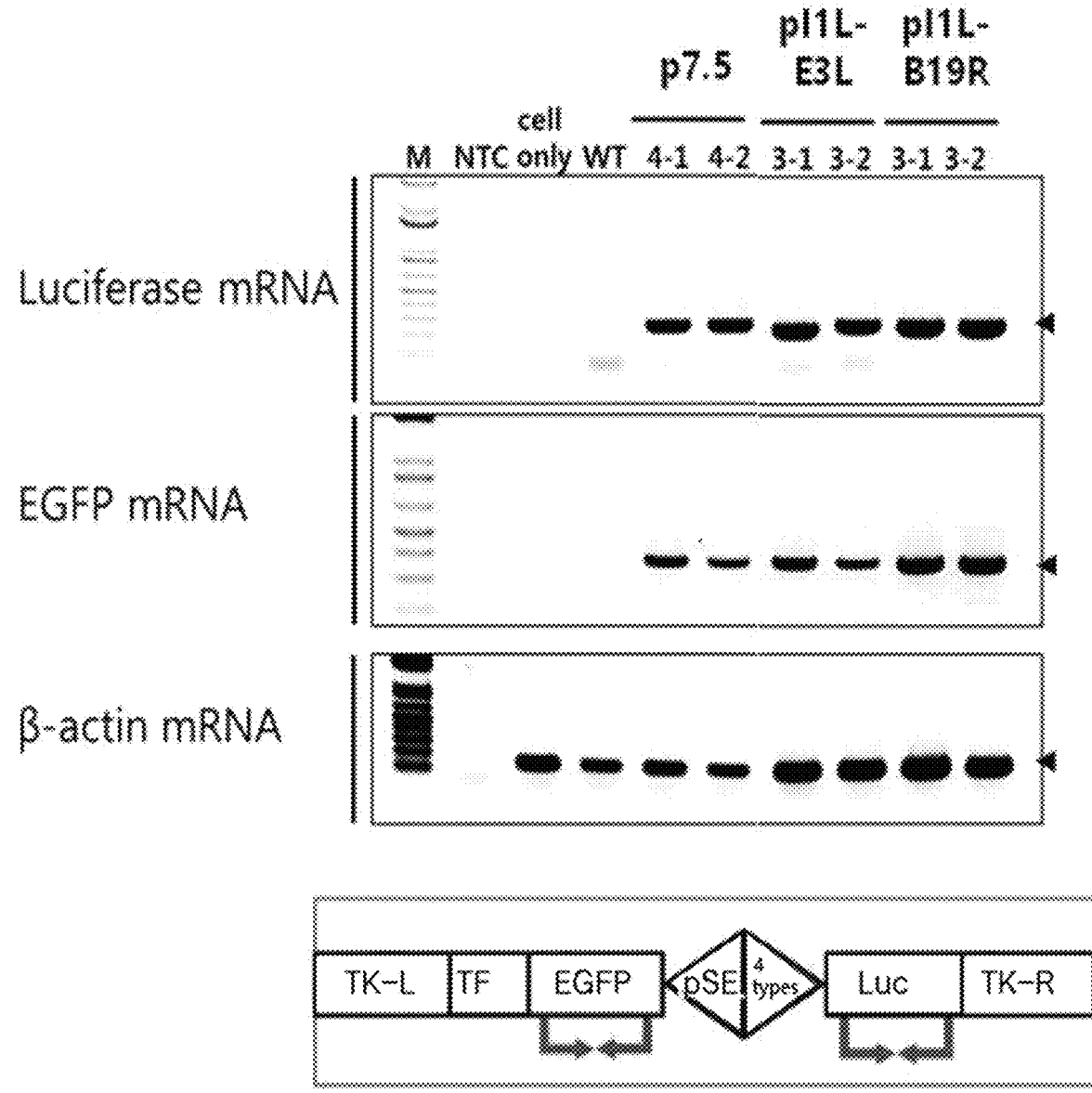

[Fig. 8]
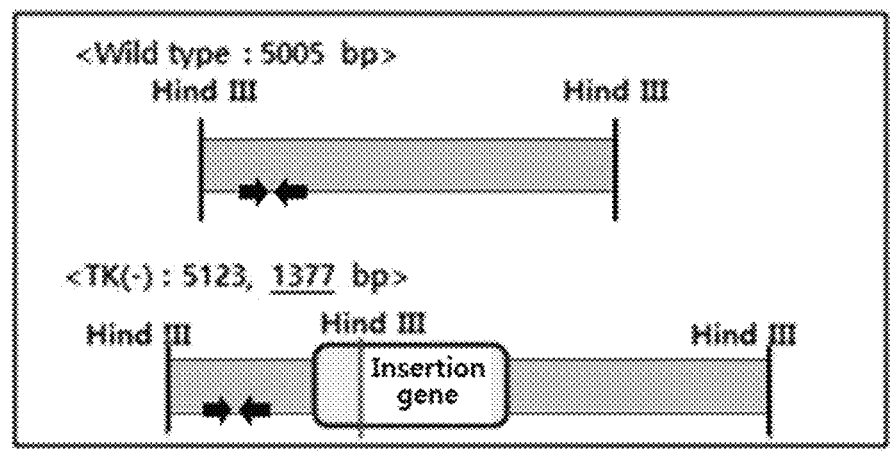
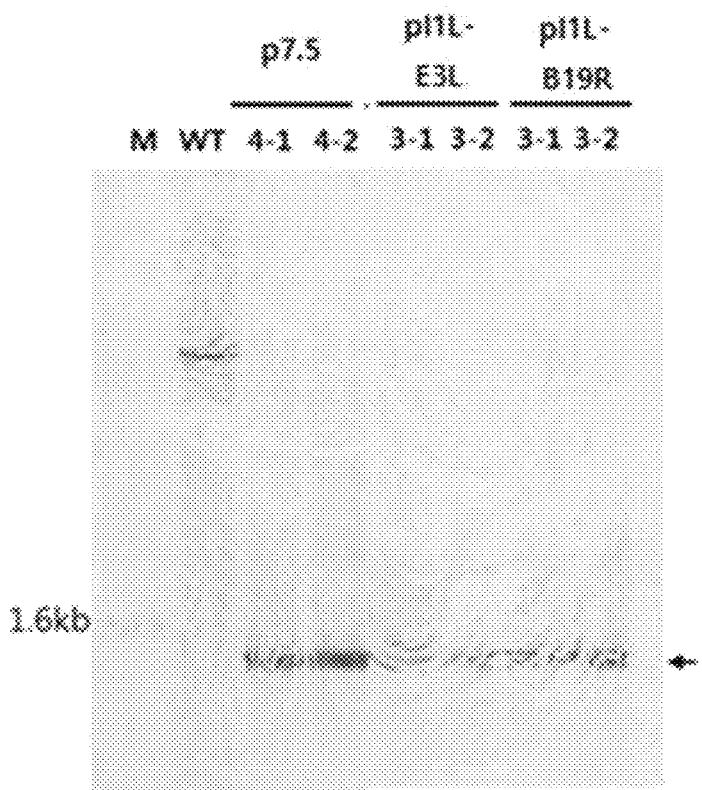

[Fig. 9]
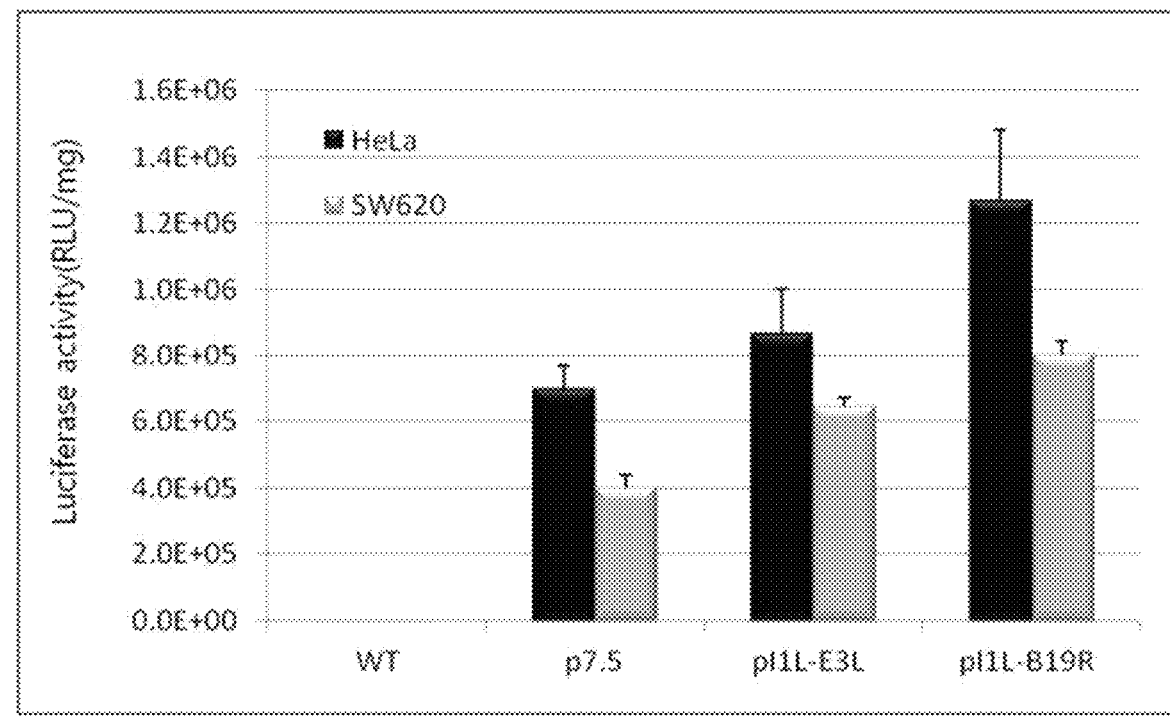
[Fig. 10a]
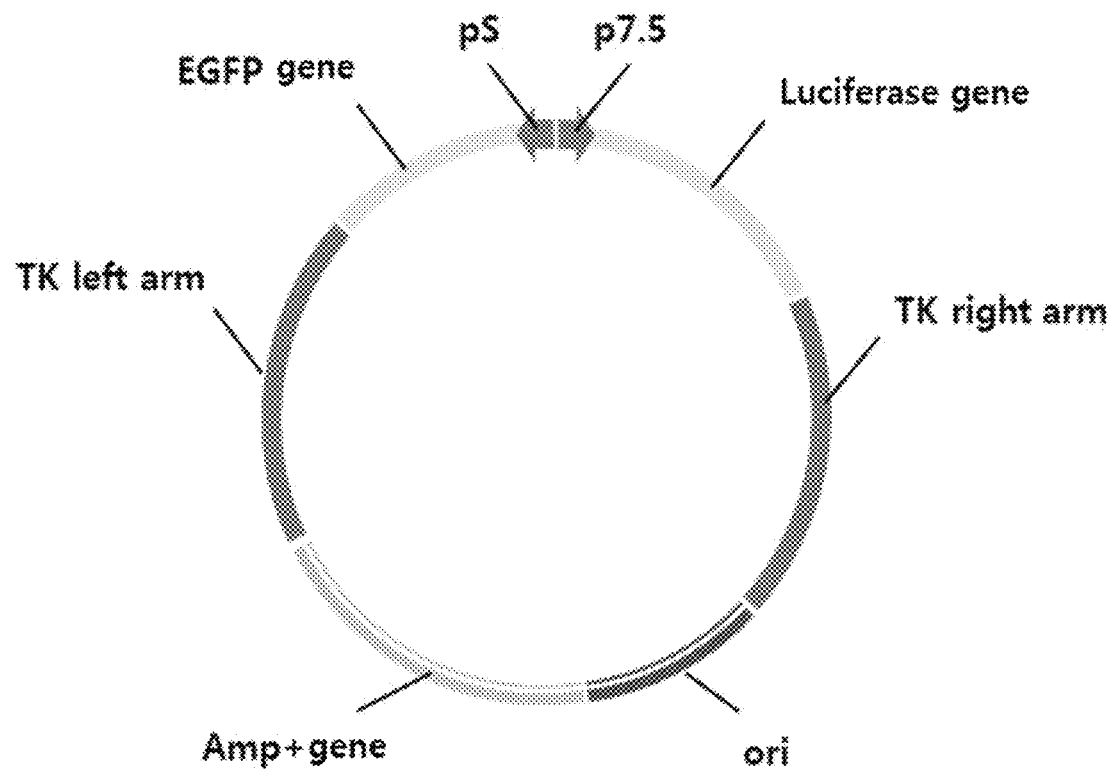

[Fig. 10b]
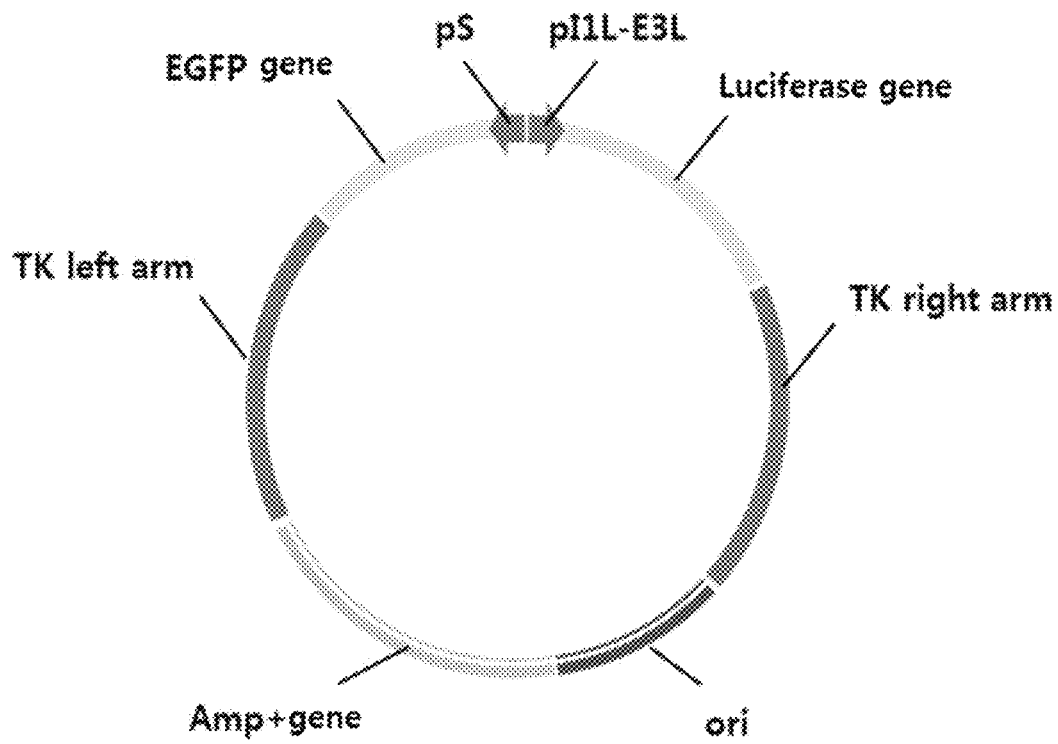
[Fig. 10c]
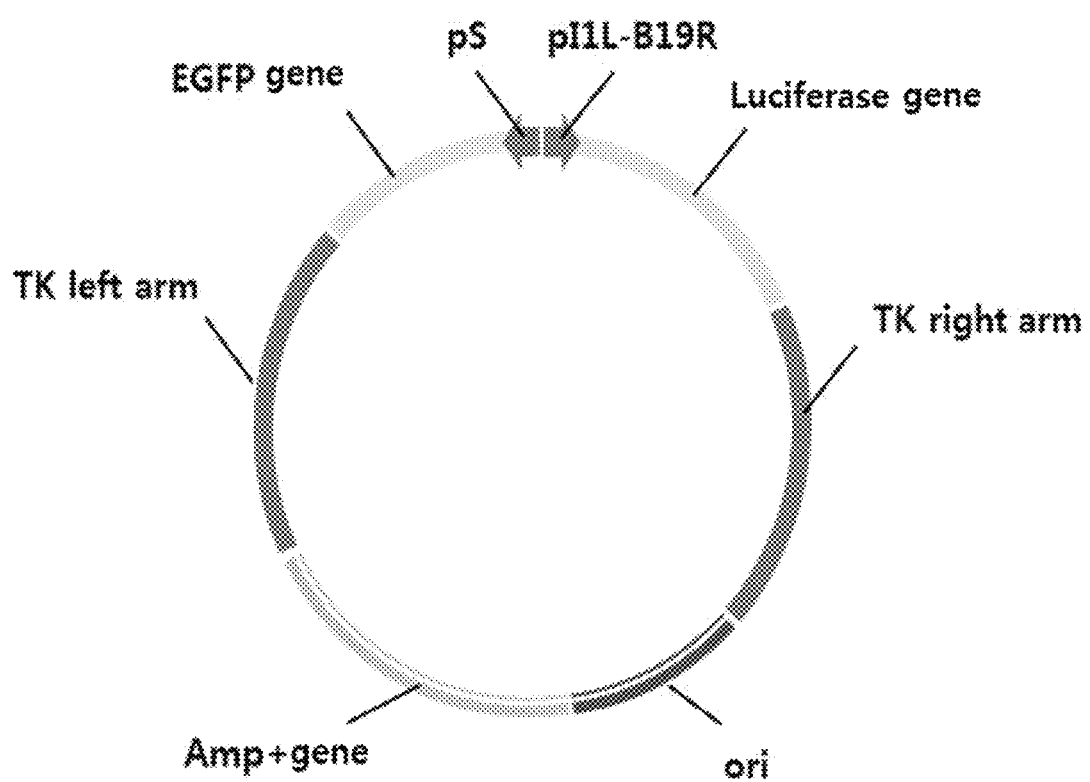

POXVIRUS-DERIVED PROMOTER, AND VECTOR COMPRISING SAME

CROSS REFERENCE TO RELATED APPLICATIONS

This application is a National Stage of International Application No. PCT/KR2016/005647, filed on May 27, 2016, which claims priority from Korean Patent Application No. 10-2015-0076197, filed on May 29, 2015, the contents of all of which are incorporated herein by reference in their entirety.

TECHNICAL FIELD

The present invention relates to a poxvirus-derived promoter, a vector comprising the promoter, a method for expressing a transgene using the promoter, and use of the vector in the prevention or treatment of a disease. The promoter according to the present invention can be used for induction of strong expression of a transgene.

BACKGROUND ART

Gene therapy is a method for treating or preventing various diseases such as genetic defects, infectious diseases, tumor, cardiovascular diseases and the like by administering genetic material such as DNA and RNA into a human body. Effective gene delivery, and induction or regulation of gene expression is important in the gene therapy. A substance used to deliver a gene into a cell is called a vector. The gene delivery vectors are largely divided into two categories, a non-viral vector and a viral vector.

As the viral vectors for gene delivery or gene expression in mammals, retroviruses, adenoviruses, adeno-associated viruses, herpes simplex viruses, lentiviruses, and poxviruses have been used. Among them, poxvirus is widely used for gene delivery and therapeutic agent development, since it has large insertion capacity, excellent gene delivery and expression efficiency, and high safety, and allows production of viruses with high titers.

Viruses belonging to poxviridae include orthopoxvirus, avipoxvirus, parapoxvirus, capripoxvirus, suipoxvirus, etc. And the viruses belonging to orthopoxvirus include smallpox virus, vaccinia virus, etc. The vaccinia virus belonging to the orthopoxvirus had been used for the prevention of smallpox and has recently been developed as a gene delivery vector using genetic engineering technology.

The main advantage of vaccinia virus vector is that large genes can be introduced as compared to other viruses (e.g., at least 10 times larger genes can be introduced as compared to adeno-associated viruses) and various cells can be infected with the virus. In addition, vaccinia virus is considered to be ideal for use as a vaccine vector since it can induce an effective immune response. For example, Bavarian Nordic company is conducting clinical trials on prostate tumor patients using MVA vector expressing tumor antigen such as PSA or PAP as a cancer vaccine. In addition, anthrax vaccines, hemorrhagic fever virus vaccines, and epidemic stomatitis virus vaccines, etc. have been developed. Recently, vaccinia virus has also been developed as an oncolytic virus and is under investigation in clinical trials. As an example, JX-594, an oncolytic virus, has been developed by Sillajen (old name: Jennerex) and various clinical trials thereof on liver tumor, colon tumor, pediatric tumor, and melanoma patients are undergoing or have been completed.

The ideal gene delivery vector should deliver a gene to a target cell with high transduction efficiency and exhibit a high expression level of the target gene, so that a good therapeutic effect can be achieved. Also the manipulation and production of the vector should be simple. In particular, in order to increase the therapeutic efficacy through the expression of an antigen or a therapeutic gene, the expression level of the gene must be high. For this purpose, high transduction efficiency by a gene delivery vector and high level of gene expression controlled by a strong promoter are required.

The common promoters used for the gene expression include HCMV, EF-1 alpha, CAG and PGK promoter. However, in case of poxvirus, the gene transcription takes place in the cytoplasm, and thus, the above promoters don't work in the vaccinia virus vector, and a poxvirus-derived promoter should be used. Representative poxvirus-derived promoters include p7.5, pE/L, pHyb and p11 promoters.

DISCLOSURE OF INVENTION

Technical Problem

It is an object of the present invention to provide a gene expression-regulating nucleic acid molecule for poxvirus which is capable of expressing a target gene at a high expression level.

It is still another object of the present invention to provide a vector comprising a gene expression-regulating nucleic acid molecule.

It is a further object of the present invention to provide a composition comprising a vector in which a gene expression-regulating nucleic acid molecule and a target gene linked to the nucleic acid molecule are introduced, and use of the composition for the treatment or prevention of a disease.

Solution to Problem

The present invention relates to a poxvirus-derived promoter which can strongly induce expression of a target gene, a plasmid vector comprising the promoter, and a poxvirus vector obtained by homologous recombination of the plasmid vector with the poxvirus (including mutant poxvirus), and a method for generating them. It also relates to a use of an antitumor drug or a vaccine which is a poxvirus vector into which a therapeutic gene or antigen was introduced.

The gene expression-regulating nucleic acid molecule, i.e., a promoter, according to the present invention refers to a promoter which can induce a high level of gene expression, compared to known other poxvirus promoters. Therefore, when they are used in a poxvirus vector, the expression level of the target gene under the control of the promoter can be increased, and the therapeutic effect of the vector containing the promoter can be enhanced. When a poxvirus vector, preferably a vaccinia virus vector is used for the gene therapy, the selection of the promoter is important for enhancing the expression of a gene delivered by the vector.

Hereinafter, the present invention will be described in more detail.

In one aspect of the present invention, there is provided a gene expression-regulating nucleic acid molecule (i.e., a promoter) derived from poxvirus, e.g., vaccinia virus, which can express a target gene with high efficiency.

The promoter according to the present invention may be a nucleic acid molecule comprising two or more polynucleotides selected from the group consisting of the polynucleotides of SEQ ID NO: 1, SEQ ID NO: 2 and SEQ ID NO: 3. Also, it may be a nucleic acid molecule comprising the polynucleotide of SEQ ID NO: 1; and one or more polynucleotides selected from the group consisting of the polynucleotides of SEQ ID NO: 2 and SEQ ID NO: 3. It may be a nucleic acid molecule formed by combining and linking two or more different polynucleotides selected from the group consisting of the polynucleotides of SEQ ID NO: 1, SEQ ID NO: 2 and SEQ ID NO: 3. For example, the nucleic acid molecule according to the present invention may be, in a 5' to 3' direction, the fusion nucleic acid molecule of SEQ ID NO: 1 and SEQ ID NO: 2, a fusion nucleic acid molecule of SEQ ID NO: 1 and SEQ ID NO: 3, a fusion nucleic acid molecule of SEQ ID NO: 1, SEQ ID NO: 2 and SEQ ID NO: 3, a fusion nucleic acid molecule of SEQ ID NO: 1, SEQ ID NO: 3 and SEQ ID NO: 2, a fusion nucleic acid molecule of SEQ ID NO: 2 and SEQ ID NO: 1, a fusion nucleic acid molecule of SEQ ID NO: 2, SEQ ID NO: 1 and SEQ ID NO: 3, and a fusion nucleic acid molecule of SEQ ID NO: 2, SEQ ID NO: 3 and SEQ ID NO: 1.

The nucleic acid molecule of SEQ ID NO: 1 is derived from the I1L gene promoter of vaccinia virus and comprises the nucleic acid sequence shown in Table 1 below. The nucleic acid molecule of SEQ ID NO: 2 is derived from the E3L gene promoter of vaccinia virus and comprises the nucleic acid sequence shown in Table 1 below. The nucleic acid molecule of SEQ ID NO: 3 is derived from the B19R gene promoter of vaccinia virus and comprises the nucleic acid sequence shown in Table 1 below.

In one embodiment, the nucleic acid molecule according to the present invention may comprise at least one or more polynucleotides selected from the group consisting of the polynucleotides of SEQ ID NO: 2 and SEQ ID NO: 3 which are linked to the 3'-end of the polynucleotide of SEQ ID NO: 1 in a 5' to 3' direction. For example, it may be a nucleic acid molecule comprising the polynucleotide of SEQ ID NO: 9 or 10.

TABLE 1

| Promoter Name | Sequence (5'→3') | SEQ ID NO: |
|---|---|---|
| pI1L | TTTGTATTTAAAAGTTGTTTGGTGAACTTAAATGGCGG | 1 |
| pE3L | TGAATAAAAAAATGATAAAATAAATTAGTTTTATTA | 2 |
| pB19R | TGTGTGTAAAAAAACTGATATTATATAAATATTTTAGTGCCGTATAA | 3 |
| pI1L-E3L | TTTGTATTTAAAAGTTGTTTGGTGAACTTAAATGGCGGTGAATAAAAAAATGATAAAATAAATTAGTTTTATTA | 9 |
| pI1L-B19R | TTTGTATTTAAAAGTTGTTTGGTGAACTTAAATGGCGGTGTGTGTAAAAAAACTGATATTATATAAATATTTTAGTGCCGTATAA | 10 |

As used herein, the term "poxvirus" refers to a virus belonging to the poxviridae. According to a preferred embodiment, the poxvirus according to the invention may include orthopoxvirus, avipoxvirus, parapoxvirus, capripoxvirus, and suipoxvirus, preferably orthopoxvirus, which includes smallpox virus and vaccinia virus, and more preferably vaccinia virus.

The poxvirus according to the present invention includes wild-type poxviruses or various mutant poxviruses. The mutant form of the virus may be one in which some genes have been deleted, substituted, or inserted. For example, in case of vaccinia virus, attempts have been made to develop as an antitumor drug which replicates in tumor cells only depending on the presence or absence of a specific gene. Thus, various mutant forms of the virus as well as wild-type viruses may be used.

The poxvirus vector according to the present invention further comprises a polynucleotide of a target gene.

In one embodiment of the present invention, the target gene is a gene whose expression is induced under the control of the promoter according to the present invention, and may be used for having therapeutic effects through gene delivery or gene expression. For example, the target gene may be a polynucleotide encoding a tumor antigen [e.g., MUC1, hTERT, Carcinoembryonic antigen (CEA)], an immune response inducer [e.g., Interleukin (IL)-12, granulocyte macrophage colony-stimulating factor (GM-CSF), or soluble PD-1], a tumor growth-inhibitory factor [e.g., Vascular endothelial growth factor (VEGF) inhibitor, Pyruvate kinase isozymes M2 (PKM2) inhibitor, or Pyruvate dehydrogenase kinase (PDK) inhibitor], an apoptosis-inducing factor [e.g., TRAIL, Thymidine kinase (TK), or Cytosine deaminase (CD)], or factors that may be helpful in increasing the activity of virus in tumor tissues [e.g., Matrix metalloproteinase (MMP), Hyaluronidase, or Relaxin].

The promoter according to the present invention is a promoter which can induce transcription of a target gene in a mammalian cell, and preferably a promoter which can induce transcription of a target gene in the cytoplasm of a mammalian cell.

In a further embodiment of the present invention, there is provided a vector comprising a promoter according to the present invention.

The vector may further comprise a target gene linked to the promoter. The vector may further comprise a gene such as EGFP, DsRed, LacZ, or GusA, which is a selection marker.

As used herein, the term "vector," "gene delivery vector," or "gene vector" refers to a substance which can deliver a transgene to a target cell or organism.

The vector encompasses both viral and non-viral vectors. The non-viral vector may be a plasmid. The viral vector may be a poxvirus vector, preferably a vaccinia virus vector.

In another embodiment of the present invention, there is provided a poxvirus vector into which a promoter according to the present invention is introduced. In a specific embodiment, there is provided a poxvirus vector constructed by homologous recombination of a plasmid vector including a promotor of the present invention with a wild-type poxvirus or various mutant poxviruses.

The recombination of the plasmid vector with the poxvirus may be carried out by a conventional method.

Another embodiment of the present invention relates to a host comprising the plasmid vector or the poxvirus vector, wherein the host may be a microorganism, a mammal, a mammalian cell, or a cell line derived from a mammal, and the mammal may be a human.

The present invention also provides a propagation method of a poxvirus vector, comprising the steps of (i) introducing a poxvirus vector according to the present invention into cells, (ii) culturing the cells under the condition suitable for allowing the poxvirus vector to be produced, and (iii) recovering the poxvirus vector from the cell culture.

The poxvirus may be recovered from the cells, but may also be recovered from the culture supernatant. One commonly used method is to disrupt cells infected with the viruses, and then collect virions in the cell lysate, and then purify the virions using techniques known in the art (chromatographic methods, ultracentrifugation methods, etc.).

The present invention also relates to a composition comprising a poxvirus according to the present invention along with a pharmaceutically acceptable excipient.

The composition according to the present invention is used for the gene therapy to prevent or treat various diseases, more specifically genetic defects, tumor, cardiovascular diseases and infectious diseases.

The present invention may be applied as a therapeutic agent or a vaccine for the prevention or treatment of various diseases by introducing a therapeutic gene or an antigen into a poxvirus vector, preferably a vaccinia virus. Also, the present invention may be used for the development of an oncolytic virus.

The composition according to the present invention may be formulated for local or parenteral administration, or digestive tract or other numerous routes of administration. For example, intragastric, subcutaneous, intracardiac, intramuscular, intravenous, intraperitoneal, intratumoral, intranasal, intrapulmonary and intrabronchial routes may be possible. The administration may be carried out as a single administration or as repeated administrations of one or more doses with a specific time interval. The appropriate route of administration and dosage may be decided depending upon various factors, such as the disease, the patient, the delivery vector, or the target gene(s) to be delivered. The drug based on viral particles according to the present invention may be formulated in the amounts of between $10^4$ and $10^{14}$ pfu (plaque-forming units), advantageously between $10^5$ and $10^{13}$ pfu, and preferably between $10^6$ and $10^{12}$ pfu.

The composition may also comprise pharmaceutically acceptable diluents, adjuvants or excipients, and solubilizers, stabilizers and preservatives. For the injection, formulations in aqueous, non-aqueous or isotonic solutions are preferred. This may be provided as a single dose or as multiple doses in a liquid or dry (powder, lyophilization, etc.) form which may be reconstituted with a suitable diluent at the time of use.

As used herein, "gene delivery" refers to the introduction (in vivo or in vitro) of a natural, synthetic, or recombinant gene or gene fragment into a cell, which is a way that the introduced gene exhibits its function. The gene or gene fragment introduced according to the present invention includes DNA or RNA having a specific sequence, or any synthetic equivalent nucleic acid.

In the present invention, the virus used for propagating a gene delivery vector may be a wild type or mutant virus. As used herein, "gene delivery efficiency" refers to the "gene delivery" efficiency of the vector, and may be detected through the evaluation of gene function as an indicator (e.g., in case of an expression vector, the expression of an encoded protein and/or the activity of its protein, etc.).

In a further aspect of the present invention there is provided a method for gene delivery into isolated animal tissues comprising the steps of propagating a gene delivery vector comprising a target gene and introducing the gene into the animal tissue through the gene delivery vector.

When the gene delivery vector according to the present invention is used as a composition for gene therapy, administration according to the present invention may be carried out by a local administration (e.g., intratumoral, intrahepatic, intramuscular, and intracerebral administration), which includes direct injection or intravascular administration (e.g., intra-arterial, intravenous, or intraportal) of a vector suspension in a solution such as PBS (phosphate buffered saline) and a saline solution.

In one embodiment, the gene delivery vectors are generally produced in unit dosage forms for injection (aqueous solutions, suspensions or emulsions), and are formulated by mixing the gene delivery vectors with pharmaceutically acceptable diluents. Herein, preferably no oxidizing agent and other ingredients known to be harmful to the gene delivery vector are included in the production. The pharmaceutical composition comprising the gene delivery vector is generally stored in an aqueous solution or lyophilized form in an ample or a vial sealed with a container having a single or multi-dose units.

In addition, the present invention provides a pharmaceutical package or kit comprising one or more containers filled with one or more of the pharmaceutical compositions according to the present invention. Furthermore, the vector according to the invention may be used together with other therapeutic compounds.

The pharmaceutical composition comprising the gene delivery vector according to the present invention may be administered to a patient in accordance with the optimal clinical design taking into account clinical conditions (i.e., the condition to be prevented or treated) of the patient, the delivery site of the composition comprising the gene delivery vector, target tissue, administration methods, administration schedules and other factors known in the art. Thus, an "effective amount" or a suitable dosage of the gene delivery vector described in the present invention is determined based on these considerations.

Advantageous Effects of Invention

The present invention relates to a promoter for poxvirus, a viral vector comprising the promoter, a use of the viral vector in the treatment and prevention of a disease. The efficacy of a therapeutic agent can be enhanced by high level of gene expression.

BRIEF DESCRIPTION OF DRAWINGS

FIG. 1 is a graph showing the comparison of the protein expression levels of luciferase after transfection of a human cervical cancer cell (HeLa cell) with plasmids containing single promoters according to Example 1.

FIG. 2 is a graph showing the comparison of the expression levels of luciferase after transfection of a human cervical cancer cell (HeLa cell) with plasmids containing recombinant promoters, i.e., pGL4.10-pI1 L-E3L, pGL4.10-pI1L-B19R, and pGL4.10-pI1L-I1L according to Example 2.

FIG. 3 shows the size of DNA fragments of pSP72-p7.5-Luc obtained by introducing p7.5 promoter (a control group) into a vaccinia virus TK (−) shuttle vector, which was treated with the DNA restriction enzymes NheI or BamHI/EcoRI.

FIG. 4 shows the size of DNA fragments of pSP72-pI1L-E3L-Luc obtained by introducing I1L-E3L promoter of Example 3 into a vaccinia viruses TK (−) shuttle vector, which was treated with restriction enzymes NheI/HindIII at the same time.

FIG. 5 shows the size of DNA fragments of pSP72-pI1 L-B19R-Luc obtained by introducing I1L-B19R promoter of Example 3 into a vaccinia viruses TK (−) shuttle vector, which was treated with restriction enzymes NheI/HindIII at the same time.

FIG. 6 shows the PCR confirmation of the genomic DNA of vaccinia viruses TK(−)-p7.5-Luc, TK(−)-pI1L-E3L-Luc, and TK(−)-pI1L-B19R-Luc into which a control group promoter or the recombinant promoter obtained in Example 3 is introduced.

FIG. 7 shows the mRNA expression levels of luciferase, GFP and beta actin, confirmed by RT-PCR, of vaccinia viruses TK(−)-p7.5-Luc, TK(−)-pI1L-E3L-Luc, and TK(−)-pI1L-B19R-Luc into which a control group promoter or the recombinant promoter obtained in Example 3 is introduced.

FIG. 8 shows the result of southern blot for confirmation of genomic DNA, of vaccinia viruses TK(−)-p7.5-Luc, TK(−)-pI1L-E3L-Luc, and TK(−)-pI1L-B19R-Luc into which a control group promoter or the recombinant promoter obtained in Example 3 is introduced.

FIG. 9 shows comparative analysis of the luciferase expression levels in a human cervical cancer cell line HeLa or a human colorectal cancer cell line SW620 treated with vaccinia viruses TK(−)-p7.5-Luc, TK(−)-pI1L-E3L-Luc, and TK(−)-pI1L-B19R-Luc into which a control group promoter or the recombinant promoter obtained in Example 3 is introduced.

FIGS. 10a to 10c depict vector map of vaccinia viruses TK(−)-p7.5-Luc, TK(−)-pI1L-E3L-Luc, and TK(−)-pI1L-B19R-Luc constructed by introducing thereinto a control group promoter or the recombinant promoter obtained in Example 3.

BEST MODE FOR CARRYING OUT THE INVENTION

Hereinafter, the present invention is explained in detail by Examples. The following Examples are intended to further illustrate the present invention without limiting its scope.

EXAMPLE 1

Preparation of Promoters 1-1: Acquisition of Promoter Genes and Construction of Plasmids Each promoter was obtained through gene synthesis. The nucleotide sequence was as follows, gene synthesis was commissioned to Macrogen, and MM192E from Bioautomation, Inc. was used as a synthesizer. The promoter gene was based on the WR genomic DNA sequence (GenBank: AY243312.1), and the sequences of each promoter are shown in Table 2 below.

TABLE 2

| Promoter Name | Sequence (5'→3') | SEQ ID NO: |
|---|---|---|
| pI1L | TTTGTATTTAAAAGTTGTTTGGTGAACTTAAATGGCGG | 1 |
| pE3L | TGAATAAAAAAATGATAAAATAAATTAGTTTTATTA | 2 |
| pB19R | TGTGTGTAAAAAAACTGATATTATATAAATATTTTAGTGCCGTATAA | 3 |
| pF11L | GGTAAAATTATATAAAAGTGAAAAACAATATTATTTTTATCGTTGGTTGTTT | 4 |
| pC11R | AATTAACAATATATTATAGTTTATATTACTGAATTAATAATATAAAATTCCCA | 5 |
| p7.5 | TCCAAACCCACCCGCTTTTTATAGTAAGTTTTTCACCCATAAATAATAAATACAATAATTAATTTCTCGTAAAAGTAGAAAATATATTCTAATTTATTGCACGG | 6 |
| pE/L | AAAATTGAAATTTTATTTTTTTTTTTGGAATATAAATAGCTAGCTCGAG | 7 |

TABLE 2-continued

| Promoter Name | Sequence (5'→3') | SEQ ID NO: |
|---|---|---|
| p11 | ATATAGTAGAATTTCATTTTGTTTTTTTCTATGCTATAAAT | 8 |

For the plasmid construction, KpnI and XhoI sequences were added to the ends of the pE/L and pI1L promoter sequences, and NheI and HindIII sequences were added to the ends of the other promoter sequences. Each of the pE/L and pI1L promoter genes was inserted into pGL4.10 [luc2] vector (Promega, USA) digested with KpnI and XhoI, and plasmids pGL4.10-pE/L and pGL4.10-pI1L were obtained.

The p7.5, p11, pE3L, pC11R, pF11L and pB19R promoter genes were inserted into pGL4.10 [luc2] vectors digested with NheI and HindIII, respectively, and the plasmids pGL4.10-p7.5, pGL4.10-p11, pGL4.10-pE3L, pGL4.10-pC11R, pGL4.10-pF11L and pGL4.10-pB19R were generated.

1-2: Evaluation of Activity of Single Promoter

The amount of luciferase protein expressed in each of the eight kinds of plasmids generated in Example 1-1 was measured to evaluate the promoter activity. Plasmids comprising pI1L, pE3L, pC11R, pF11L, and pB19R promoters, and plasmids containing known p7.5, pE/L and p11 promoters as a control group were used.

In order to examine the promoter activity of the plasmids, HeLa cells were transfected with plasmids, each of which contains one of the eight kinds of promoters prepared in Example 1-1, and then the amounts of expression of luciferase were determined. HeLa cells were cultured in a MEM medium supplemented with 10% fetal bovine serum and inoculated on a 24 well culture plate at $6 \times 10^4$ cells/well. The next day, the cells were infected with vaccinia virus, and after 6 hours, the virus-infected cells were transfected with plasmids into which the virus promoter had been introduced using a transfection solution. After 24 hours, the media were removed, and a portion of the cell lysate obtained by treating the cells with cell lysis solution was transferred to a 96-well culture plate for luciferase measurement, and luciferin, which is a substrate of luciferase enzyme, was treated. The amount of light generated by substrate degradation was measured using a luciferase analyzer, and the measured results for each promoter are shown in FIG. 1. FIG. 1 shows the comparison of the expression levels of luciferase after transfection of HeLa cells, which are human cervical cancer cell lines, with plasmids containing respective promoters. p7.5, pE/L, and p11 are the promoters previously used as control groups, and pE3L, pC11R, pF11L, pB19R and pI1L are candidate promoters used in experimental groups.

As shown in FIG. 1, the expression level of the gene by the plasmid into which pI1L was introduced was about three times higher as compared with the control plasmid in which p7.5, pE/L or p11 promoter was introduced, and the amount of gene expression by the plasmid into which pE3L or pB19R was introduced was similar to that of the control group.

1-3: Acquisition of Recombinant Promoter Genes

In order to increase the activity of the promoter, recombinant promoters were generated by combining the I1L promoter, which exhibited the highest activity as a single promoter in Example 1-2, with the E3L or B19R promoter, which showed a relatively high activity. Each promoter was synthesized in the same manner as in Example 1-1, and the nucleotide sequence thereof was as follows.

TABLE 3

| Promoter Name | Sequence (5'→3') | SEQ ID NO: |
|---|---|---|
| pI1L-E3L | TTTGTATTTAAAAGTTGTTTGGTGAACTTAAATGGCGGTG AATAAAAAAATGATAAAATAAATTAGTTTTATTA | 9 |
| pI1L-B19R | TTTGTATTTAAAAGTTGTTTGGTGAACTTAAATGGCGGTG TGTGTAAAAAAACTGATATTATATAAATATTTTAGTGCCG TATAA | 10 |
| pI1L-I1L | TTTGTATTTAAAAGTTGTTTGGTGAACTTAAATGGCGGTT TGTATTTAAAAGTTGTTTGGTGAACTTAAATGGCGG | 11 |

For the plasmid construction, NheI and HindIII sequences were added to the ends of each recombinant promoter sequence.

The recombinant promoter genes pI1L-E3L, pI1L-B19R and pI1L-I1L were inserted into the pGL4.10 [luc2] vector digested with NheI and HindIII to generate plasmids pGL4.10-pI1L-E3L, pGL4.10-pI1L-B19R, and pGL4.10-pI1L-I1L.

EXAMPLE 2

Evaluation of Promoter Activity

The amount of luciferase protein expressed in the three kinds of plasmids generated in Example 1-3 was measured to evaluate the promoter activity.

Specifically, in order to examine the promoter activity of the plasmids, the expression levels of luciferase were measured after transfection of HeLa cells with the plasmids. HeLa cells cultured in MEM medium supplemented with 10% fetal bovine serum were inoculated in a 24-well culture plate at $6\times10^4$ cells per well. The next day, the cells were infected with vaccinia virus, and after 6 hours, plasmids into which the Vaccinia virus promoter was introduced were treated with virus-infected cells using a transfection solution. After 2 hours, the medium around the cells was removed, and a portion of the cell lysate obtained by treating the cell lysate was transferred to a 96-well culture plate for luciferase measurement, and luciferin, which is a substrate of luciferase enzyme, was treated. The amount of light generated by substrate degradation was measured using a luciferase analyzer, and the measured results for each promoter are shown in FIG. 2 and Table 4. FIG. 2 shows the comparison of the activities of recombinant promoters produced by combining pE3L or pB19R, which has a relatively high activity, with pI1L, which exhibited the highest activity in Example 1.

As shown in FIG. 2, the plasmid in which the recombinant promoter pI1L-E3L or pI1L-B19R was introduced showed a gene expression amount about 6 times higher than that of the plasmid in which the p7.5 promoter was introduced as a control group, and showed a gene expression amount about 2.4 times higher than that of the plasmid in which the pI1L single promoter was introduced. In addition, the pI1L-I1L plasmid prepared by combining two copies of the pI1L promoter having a high promoter activity showed the expression level increased by about 1.5 times as compared with the plasmid in which the pI1L single promoter was introduced.

TABLE 4

| Promoter | Luciferase activity (unit: RLU/mg) |
|---|---|
| Vector | 10,946 |
| p7.5 | 1,747,383 |
| pI1L | 5,337,647 |
| pI1L-E3L | 11,834,807 |
| pI1L-B19R | 12,274,591 |
| pI1L-pI1L | 8,661,349 |

In case of pI1L-I1L obtained by combining two copies of pI1L having the highest activity in Example 1-2, the activity of luciferase was U.S. Pat. No. 8,661,349, which is increased by less than twice as compared with pI1L. However, when pI1L was combined with E3L or B19R, the activity was increased by more than twice. As shown in the results of FIG. 1, the activity of p7.5 was the highest among the existing promoters, but it was confirmed from FIG. 2 that the activities of all promoters used in the experiment were higher than that of p7.5.

EXAMPLE 3

Promoter-Introduced Viral Vector 3-1: Shuttle Vector Construction for Viral Vector In order to examine whether the result of the activity evaluation of the promoter measured using the plasmid into which the recombinant promoter was introduced can be applied to viruses in the same way, the viral promoter according to the present invention and reporter gene luciferase were introduced together into the virus shuttle vector pSP72-TK(−) in which TK gene was removed.

pGL4.10-p7.5 used as a control group in Example 1-1 and pGL4.10-pI1L-E3L and pGL4.10-pI1L-B19R obtained in Example 1-3 were cut by NheI and XbaI, and promoters and luciferase genes were obtained. The genes thus obtained were inserted into pSP72-TK(−) shuttle vectors cut by NheI and XbaI, and pSP72-TK(−)-p7.5-Luc, pSP72-TK(−)-pI1L-E3L-Luc, and pSP72-TK(−)-pI1L-B19R-Luc were finally obtained.

3-2: Generation of Recombinant Vaccinia Virus

The recombinant shuttle vector prepared in Example 3-1 along with wild-type vaccinia virus was introduced into the cells to prepare a recombinant virus. Recombinant vaccinia virus was prepared by inserting into the TK gene position of vaccinia virus by homologous recombination.

Specifically, HeLa cells cultured in MEM medium supplemented with 10% fetal bovine serum were inoculated in a 6-well culture plate at $3\times10^5$ cells/well. The next day, the vaccinia virus shuttle vectors pSP72-TK(−)-p7.5-Luc, pSP72-TK(−)-pI1L-E3L-Luc, and pSP72-TK(−)-pI1L-B19R-Luc were treated with a transfection solution and vaccinia viruses were infected at 0.05 MOI, and 4 hours later, the culture medium was replaced with MEM medium supplemented with 5% fetal bovine serum, and then cultured for 48 hours. The cultured cells were removed from the medium, and frozen and thawed three times to obtain crude viruses, which were then subjected to a plaque isolation method three times to obtain a clone of pure recombinant viruses.

The virus thus obtained was measured for the potency in Vero cells using the TCID50 method, and the structure was confirmed by RT-PCR, genomic DNA PCR, sequencing and southern blot, and then used for an experiment. As a result, TK(−)-p7.5-Luc (FIG. 10a), TK(−)-pI1L-E3L-Luc (FIG. 10b), TK(−)-pI1L-B19R-Luc (FIG. 10c), which are the recombinant vaccinia viruses into which each promoter and luciferase were introduced, were finally obtained.

3-3: Measurement of Virus Potency

The concentration of infectious viruses is referred to by the diluted concentration of the viruses infecting 50% of the cultured host cells, i.e., 50% tissue culture infectious dose (TCID50). The potency of the viruses was measured using TCID50 methods, and the characteristics of the recombinant viruses were analyzed.

Specifically, Vero cells were cultured in a 96-well plate at $5 \times 10^3$ cells/well, and the viruses were respectively diluted at 1/10, $1/10^2$, $1/10^3$, $1/10^4$, $1/10^5$, $1/10^6$, $1/10^7$, and $1/10^8$ and then infected into each well. After 4 days, the number of wells in which the CPE (cytopathic effect) appeared was counted and the titer was calculated. The results of virus titration are shown in Table 5.

TABLE 5

| Virus | Titer (TCID$_{50}$/ml) |
| --- | --- |
| TK(−)-p7.5-Luc | $6.9 \times 10^7$ |
| TK(−)-pI1L-E3L-Luc | $9.4 \times 10^7$ |
| TK(−)-pI1L-B19R-Luc | $8.7 \times 10^7$ |

As shown in Table 5, all of the three recombinant viruses exhibited similar titers, indicating that they had similar productivity.

3-4: Analysis of the Structure of Recombinant Virus

To perform genomic DNA PCR, the genomic DNA of the virus was extracted and the size of the transgene inserted instead of the TK gene was confirmed by PCR. Recombination was confirmed by comparison with wild-type virus IHD-W.

The results are shown in FIG. 6. As shown in FIG. 6, it was confirmed that, in case of the wild type virus, the 966 bp fragment was amplified by the PCR, and in case of the recombinant virus, the length of the fragment amplified by gene introduction increased to 3.1~3.2 Kb, indicating that there was no abnormality in the DNA structure.

HeLa cells were cultured in 6-well culture dishes at $3 \times 10^5$ cells/well in order to perform RT-PCR of viral RNA, and the recombinant viruses that had been subjected to the above titer measurement were cultured for 48 hours after 0.05 MOI treatment. Then the cells were lysed by trizol treatment and RNA was extracted and cDNA was synthesized in vitro. The structure of the transgene was analyzed by PCR using the DNA as a template, and the recombination was confirmed. FIG. 7 indicates that mRNA of luciferase and EGFP were well expressed in all of the three kinds of recombinant viruses unlike the wild type virus into which no exogenous gene was introduced.

To perform the southern blot, HeLa cells were cultured in a 75T culture dish at $2 \times 10^6$ cells/well and the recombinant viruses that had been subjected to the above titer measurement were cultured for 72 hours after 0.05 MOI treatment. After the cell culture medium was removed, the cells were frozen and thawed three times to obtain the virus. The genomic DNA of the virus was extracted and cut with a Hind III restriction enzyme, and the bands were separated from 0.8% agarose, transferred to a nylon membrane, fixed at 120° C., and hybridized with a DIG-labeling probe. After contacting with the final substrate following washing and blocking processes, selective DNA bands were identified. The results of southern blot analysis are shown in FIG. 8.

As shown in FIG. 8, in case of the wild type virus, the probe was bound to the DNA fragment of 5005 bp, but in case of the recombinant virus, the probe was bound to the DNA fragment reduced to 1337 bp by gene introduction. Thus, it was found that there was no abnormality in the DNA structure of the site where the transgene was introduced. The site where the probe binds is indicated by a blue arrow.

EXAMPLE 4

Evaluation of Protein Expression Level by Recombinant Virus

The recombinant vaccinia viruses TK(−)-p7.5-Luc, TK(−)-pI1L-E3L-Luc, TK(−)-pI1L-B19R-Luc constructed in Example 3-2 were infected to human cervical cancer cell line HeLa or human colon cancer cell line SW620, and the expression levels of luciferase regulated by respective promoters were analyzed.

Specifically, HeLa cells or SW620 cells cultured in MEM medium supplemented with 10% fetal bovine serum were inoculated in a 12-well culture plate at $2 \times 10^5$ cells/well. The following day, they were infected with each of the recombinant viruses (wild-type WT, p7.5, I1L-E3L, and I1L-B19R) at 1 MOI. After 6 hours, the culture medium surrounding the cells was removed and cell lysis solution was added. A portion of the cell lysates was transferred to a 96-well culture plate for luciferase measurement, and treated with luciferin, which is a substrate of luciferase enzyme. The amount of light generated by substrate degradation was measured using a luciferase analyzer, and the results are shown in FIG. 9. FIG. 9 shows the results of analysis of the expression levels of luciferase after the human cervical cancer cell line HeLa or human colon cancer cell line SW620 were infected with the recombinant vaccinia viruses TK(−)-p7.5-Luc, TK(−)-pI1L-E3L-Luc, and TK(−)-pI1L-B19R-Luc.

As shown in FIG. 9, the luciferase expression levels by the recombinant virus containing pI1L-B19R promoter in both HeLa and SW620 were about twice as high as that of the control virus containing p7.5 promoter.

The invention claimed is:

1. A recombinant nucleic acid molecule consisting of two or three different polynucleotides selected from the group consisting of the polynucleotides of SEQ ID NO: 1, SEQ ID NO: 2 and SEQ ID NO: 3,
   wherein the two or three polynucleotides are consecutively linked in 5' to 3' direction in a way that 3'-end of an immediate preceding polynucleotide is linked to 5'-end of a next polynucleotide.

2. The recombinant nucleic acid molecule according to claim 1, consisting of:
   the polynucleotide of SEQ ID NO: 1; and
   one or two polynucleotides selected from the group consisting of the polynucleotides of SEQ ID NO: 2 and SEQ ID NO: 3.

3. The recombinant nucleic acid molecule according to claim 2, wherein the one or two polynucleotides selected from the group consisting of the polynucleotides of SEQ ID NO: 2 and SEQ ID NO: 3 is/are linked to the 3'-end of the polynucleotide of SEQ ID NO: 1 in a 5' to 3' direction.

4. A recombinant nucleic acid construct consisting of (a) the recombinant nucleic acid molecule according to claim 2 and (b) a restriction enzyme recognition site at the 5'-end and/or 3'-end of the recombinant nucleic acid molecule.

5. The recombinant nucleic acid molecule according to claim 1, comprising the nucleotide sequence of SEQ ID NO: 9 or SEQ ID NO: 10.

6. A recombinant nucleic acid construct consisting of (a) the recombinant nucleic acid molecule according to claim 1 and (b) a nucleotide encoding a target protein, so as to induce expression of the target protein-encoding nucleotide sequence in a host cell.

7. The recombinant nucleic acid construct according to claim 6, wherein the host cell is a mammalian cell and the target protein is expressed in cytoplasm of the mammalian cell.

8. A vector comprising the recombinant nucleic acid molecule according to claim 1.

9. The vector according to claim 8, which is a virus.

10. The vector according to claim 9, which is derived from a virus of a poxviridae.

11. The vector according to claim 10, wherein the virus of the poxviridae is selected from the group consisting of the viruses of orthopoxvirus, avipoxvirus, parapoxvirus, capripoxvirus, and suipoxvirus genuses.

12. The vector according to claim 10, wherein the poxvirus is vaccinia virus.

13. A vector comprising the recombinant nucleic acid construct according to claim 6.

14. The vector according to claim 13, wherein the target protein is a tumor antigen, an immune response-inducing factor, a tumor growth-inhibitory factor, an apoptosis-inducing factor, or a factor which can aid in enhancing an activity of a virus in a tumor tissue.

15. A host transformed with a vector comprising the recombinant nucleic acid molecule according to claim 1.

16. The host according to claim 15, which is a microorganism, a mammal, a mammalian cell, or a cell line derived from a mammal.

17. A vector comprising the recombinant nucleic acid molecule according to claim 5.

18. A vector comprising the recombinant nucleic acid construct according to claim 4.

19. A vector comprising the recombinant nucleic acid molecule according to claim 3.

20. A vector comprising the recombinant nucleic acid molecule according to claim 2.

\* \* \* \* \*

SEQUENCE LISTING

<160> NUMBER OF SEQ ID NOS: 11

<210> SEQ ID NO 1

-continued

```
<211> LENGTH: 38
<212> TYPE: DNA
<213> ORGANISM: Artificial Sequence
<220> FEATURE:
<223> OTHER INFORMATION: pI1L promoter

<400> SEQUENCE: 1
tttgtattta aaagttgttt ggtgaactta aatggcgg                               38

<210> SEQ ID NO 2
<211> LENGTH: 37
<212> TYPE: DNA
<213> ORGANISM: Artificial Sequence
<220> FEATURE:
<223> OTHER INFORMATION: pE3L promoter

<400> SEQUENCE: 2
tgaataaaaa aaatgataaa ataaattagt tttatta                               37

<210> SEQ ID NO 3
<211> LENGTH: 47
<212> TYPE: DNA
<213> ORGANISM: Artificial Sequence
<220> FEATURE:
<223> OTHER INFORMATION: pB19R promoter

<400> SEQUENCE: 3
tgtgtgtaaa aaaactgata ttatataaat attttagtgc cgtataa                    47

<210> SEQ ID NO 4
<211> LENGTH: 53
<212> TYPE: DNA
<213> ORGANISM: Artificial Sequence
<220> FEATURE:
<223> OTHER INFORMATION: pF11L promoter

<400> SEQUENCE: 4
ggtaaaatta tataaaaagt gaaaaacaat attattttta tcgttggttg ttt             53

<210> SEQ ID NO 5
<211> LENGTH: 53
<212> TYPE: DNA
<213> ORGANISM: Artificial Sequence
<220> FEATURE:
<223> OTHER INFORMATION: pC11R promoter

<400> SEQUENCE: 5
aattaacaat atattatagt ttatattact gaattaataa tataaaattc cca             53

<210> SEQ ID NO 6
<211> LENGTH: 104
<212> TYPE: DNA
<213> ORGANISM: Artificial Sequence
<220> FEATURE:
<223> OTHER INFORMATION: p7.5 promoter

<400> SEQUENCE: 6
tccaaaccca cccgcttttt atagtaagtt tttcacccat aaataataaa tacaataatt      60
aatttctcgt aaaagtagaa aatatattct aatttattgc acgg                      104

<210> SEQ ID NO 7
<211> LENGTH: 50
<212> TYPE: DNA
<213> ORGANISM: Artificial Sequence
<220> FEATURE:
<223> OTHER INFORMATION: pE/L promoter
```

```
<400> SEQUENCE: 7
aaaattgaaa ttttattttt tttttttgga atataaatag ctagctcgag                50

<210> SEQ ID NO 8
<211> LENGTH: 41
<212> TYPE: DNA
<213> ORGANISM: Artificial Sequence
<220> FEATURE:
<223> OTHER INFORMATION: p11 promoter

<400> SEQUENCE: 8
atatagtaga atttcattt gtttttttct atgctataaa t                          41

<210> SEQ ID NO 9
<211> LENGTH: 75
<212> TYPE: DNA
<213> ORGANISM: Artificial Sequence
<220> FEATURE:
<223> OTHER INFORMATION: pI1L-E3L promoter

<400> SEQUENCE: 9
tttgtattta aaagttgttt ggtgaactta aatggcggtg aataaaaaaa atgataaaat      60
aaattagttt tatta                                                      75

<210> SEQ ID NO 10
<211> LENGTH: 85
<212> TYPE: DNA
<213> ORGANISM: Artificial Sequence
<220> FEATURE:
<223> OTHER INFORMATION: pI1L-B19R promoter

<400> SEQUENCE: 10
tttgtattta aaagttgttt ggtgaactta aatggcggtg tgtgtaaaaa aactgatatt      60
atataaatat tttagtgccg tataa                                           85

<210> SEQ ID NO 11
<211> LENGTH: 76
<212> TYPE: DNA
<213> ORGANISM: Artificial Sequence
<220> FEATURE:
<223> OTHER INFORMATION: pI1L-I1L promoter

<400> SEQUENCE: 11
tttgtattta aaagttgttt ggtgaactta aatggcggtt tgtatttaaa agttgtttgg      60
tgaacttaaa tggcgg                                                     76
```